(12) United States Patent
Hsu

(10) Patent No.: US 8,808,239 B2
(45) Date of Patent: Aug. 19, 2014

(54) SYRINGE

(71) Applicant: Kuo-Chi Hsu, Changhua (TW)

(72) Inventor: Kuo-Chi Hsu, Changhua (TW)

( * ) Notice: Subject to any disclaimer, the term of this patent is extended or adjusted under 35 U.S.C. 154(b) by 0 days.

(21) Appl. No.: 14/070,563

(22) Filed: Nov. 3, 2013

(65) Prior Publication Data

US 2014/0058325 A1    Feb. 27, 2014

Related U.S. Application Data

(63) Continuation of application No. 13/531,648, filed on Jun. 25, 2012, now abandoned.

(51) Int. Cl.
   *A61M 5/50*       (2006.01)

(52) U.S. Cl.
   CPC .................................. *A61M 5/5066* (2013.01)
   USPC ........................................... 604/110; 604/195

(58) Field of Classification Search
   USPC ........................................ 604/110, 111, 195
   See application file for complete search history.

(56) References Cited

U.S. PATENT DOCUMENTS

| | | | | |
|---|---|---|---|---|
| 4,747,830 A | * | 5/1988 | Gloyer et al. | 604/110 |
| 5,575,774 A | * | 11/1996 | Chen | 604/110 |
| 2006/0052748 A1 | * | 3/2006 | Coelho et al. | 604/110 |
| 2006/0264826 A1 | * | 11/2006 | Chen | 604/110 |
| 2007/0078407 A1 | * | 4/2007 | Huang | 604/198 |
| 2007/0149923 A1 | * | 6/2007 | Chen | 604/110 |
| 2007/0250015 A1 | * | 10/2007 | Lee et al. | 604/195 |
| 2012/0191041 A1 | * | 7/2012 | Pullara | 604/110 |
| 2012/0226241 A1 | * | 9/2012 | Chang | 604/228 |

* cited by examiner

*Primary Examiner* — Nicholas Lucchesi
*Assistant Examiner* — Gerald Landry, II
(74) *Attorney, Agent, or Firm* — Che-Yang Chen; Law Office of Michael Chen

(57) ABSTRACT

A syringe includes a needle, a barrel and a push rod inserted in the barrel. The needle includes a needle seat, a stop ring fitted on an outer wall of the needle seat, and a check groove formed on the inner wall of the needle seat. The check groove is adapted to engage with a check rib on a core post of the push rod. A resilient plug is provided in the barrel. The resilient plug has a central through hole for insertion of the core post of a push head of the push rod. The push rod has a frangible point at a front end thereof. When the push rod is pulled backward, the needle is received in the barrel completely and the rear section of the push rod can be broken.

1 Claim, 5 Drawing Sheets

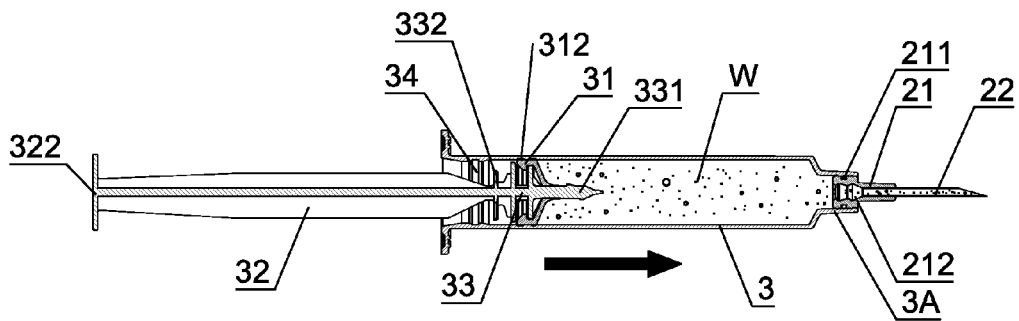
Fig. 3-A
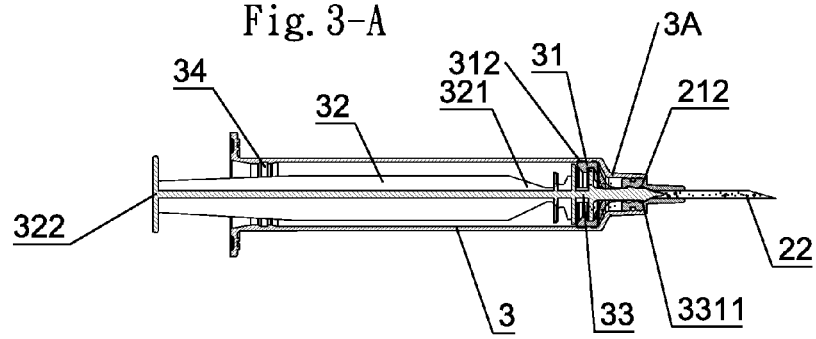
Fig. 3-B
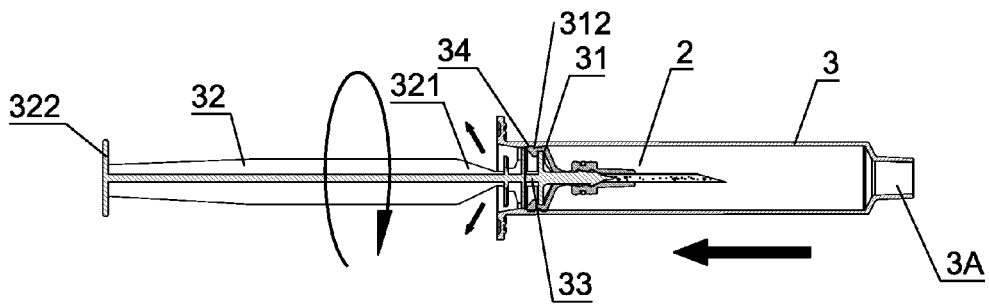
Fig. 3-C
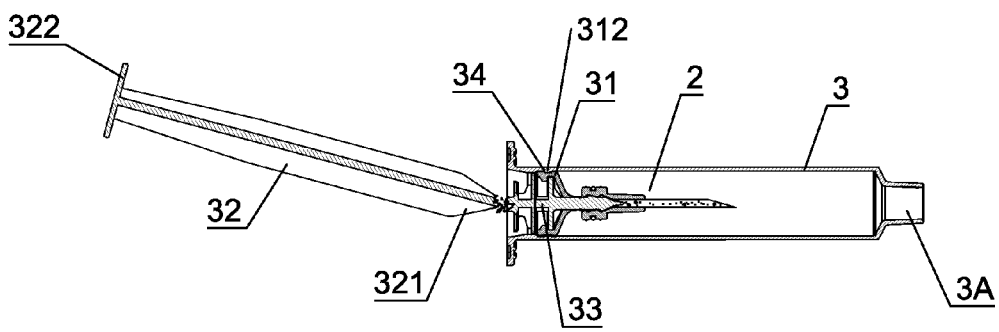
Fig. 3-D

SYRINGE

BACKGROUND OF THE INVENTION

1. Field of the Invention

The present invention relates to a syringe, and more particularly, to a syringe having a push head provided at the front end of a push rod. The push rod has a core post protruding from a front end thereof to be engaged in a needle seat. After injection, the push rod is pulled backward to retract the needle in a barrel and the rear section of the push rod is broken. Thus, the needle is completely received and positioned in the barrel for safety. The present invention has a simple configuration and can be operated conveniently, without the need of additional parts.

2. Description of the Prior Art

The needle of a medical syringe is direct contact with the skin of the patient, having the problem of infection. After use, the most important issue of the syringe is how to avoid the needle from poking other persons. As shown in FIG. 5 and FIG. 6, a conventional syringe 4 has a cover 41 to protect a needle 42. Before injection, the needle 42 is protected by the cover 41. When in use, the cover 41 is pulled away. After injection, the needle 42 is protected by the cover 41 again. After use, the syringe 4 must be collected. During collection, the cover may disengage from the syringe by collision, so the needle will be exposed to cause dangers.

To overcome the aforesaid shortcomings, safe syringes are developed, such as M411948 TW (as shown in FIGS. 7) and M363918 TW (as shown in FIG. 8). The needle is moved backward to be received in the barrel. The configuration of this safe syringe is complicated and it cannot be used conveniently. The syringe may have operation trouble sometimes.

For consideration to the cost, the entire barrel must be thrown away after use and the syringe has many parts, so it is not cost-effective.

Accordingly, the present invention intends to provide a syringe for improving the shortcomings mentioned above.

SUMMARY OF THE INVENTION

The primary object of the present invention is to provide a syringe which comprises a needle, a barrel and a push rod inserted in the barrel. The push rod comprises a push head at a front end thereof. The push head can be pushed in the central through hole of a resilient plug. A core post protrudes from the center of the push head. A check rib is formed on an outer surface of the core post. After injection, the pushed head is pushed into the needle seat and the check rib engages with a check groove of the needle to be positioned thereat. The push rod is pulled backward to retract the needle in the barrel, and then the push rod is turned and broken at the frangible point to be thrown away. The operation to retract the needle is simple and convenient, and the manufacture cost is lowered.

A further object of the present invention is to provide a syringe, wherein a resilient plug is provided in the barrel. The resilient plug has an annular protruding portion at a rear end thereof. When the push rod is pulled backward, the annular protruding portion is engaged in an annular recess formed on the inner wall of the rear end of the barrel, such that the push rod is positioned thereat for the user to break the rear section of the push rod conveniently. The front end of the push rod, the resilient plug and the needle are received in the barrel, enhancing the safety of the syringe.

A still further object of the present invention is to provide a syringe, wherein the rear section of the push rod and the barrel having the needle therein can be thrown away separately. The damaged appearance of the syringe can be identified explicitly, preventing stab wound or contact by accident.

BRIEF DESCRIPTION OF THE DRAWINGS

FIG. 3A and FIG. 3B are schematic views showing the present invention in an injection state;

FIG. 3C is a schematic view showing the needle received in the barrel of present invention;

FIG. 3D is a schematic view showing the push rod of present invention being broken;

DETAILED DESCRIPTION OF THE PREFERRED EMBODIMENTS

Embodiments of the present invention will now be described, by way of example only, with reference to the accompanying drawings.

Figure 1:
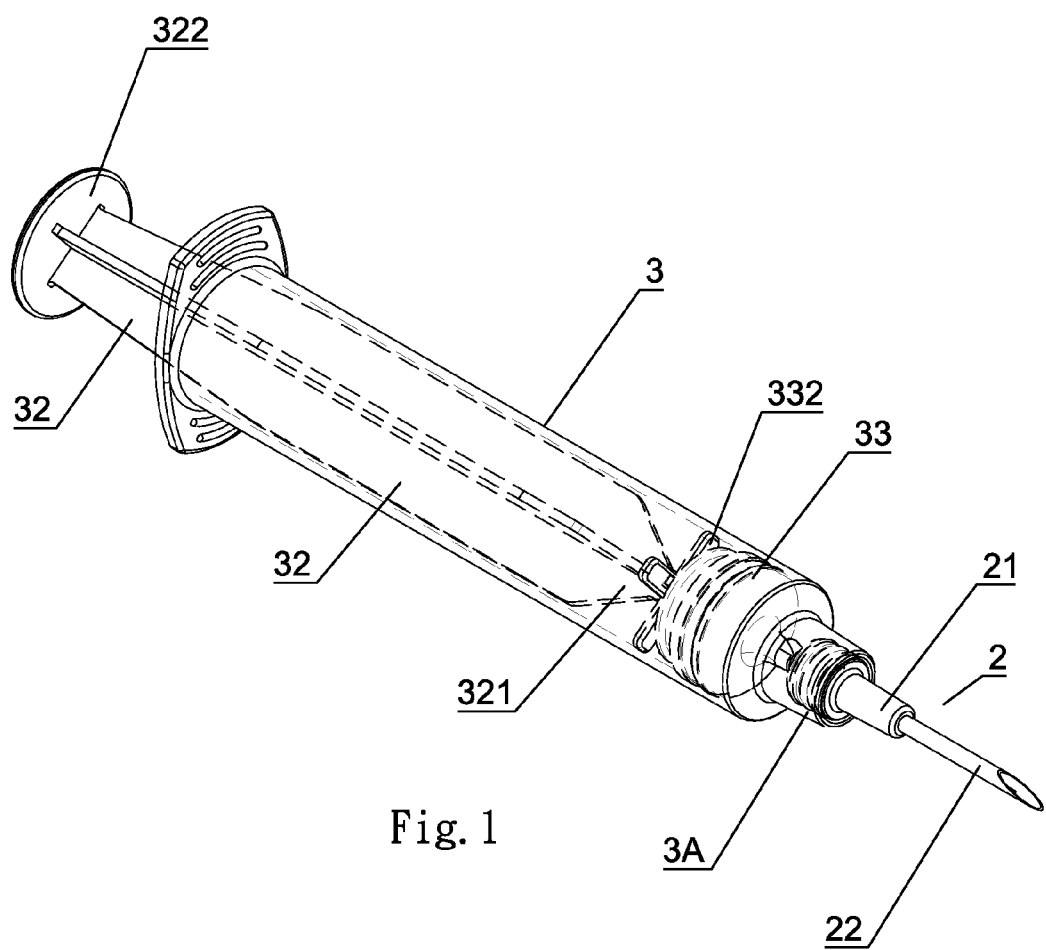
FIG. 1 is a perspective view of the present invention.
Figure 2:
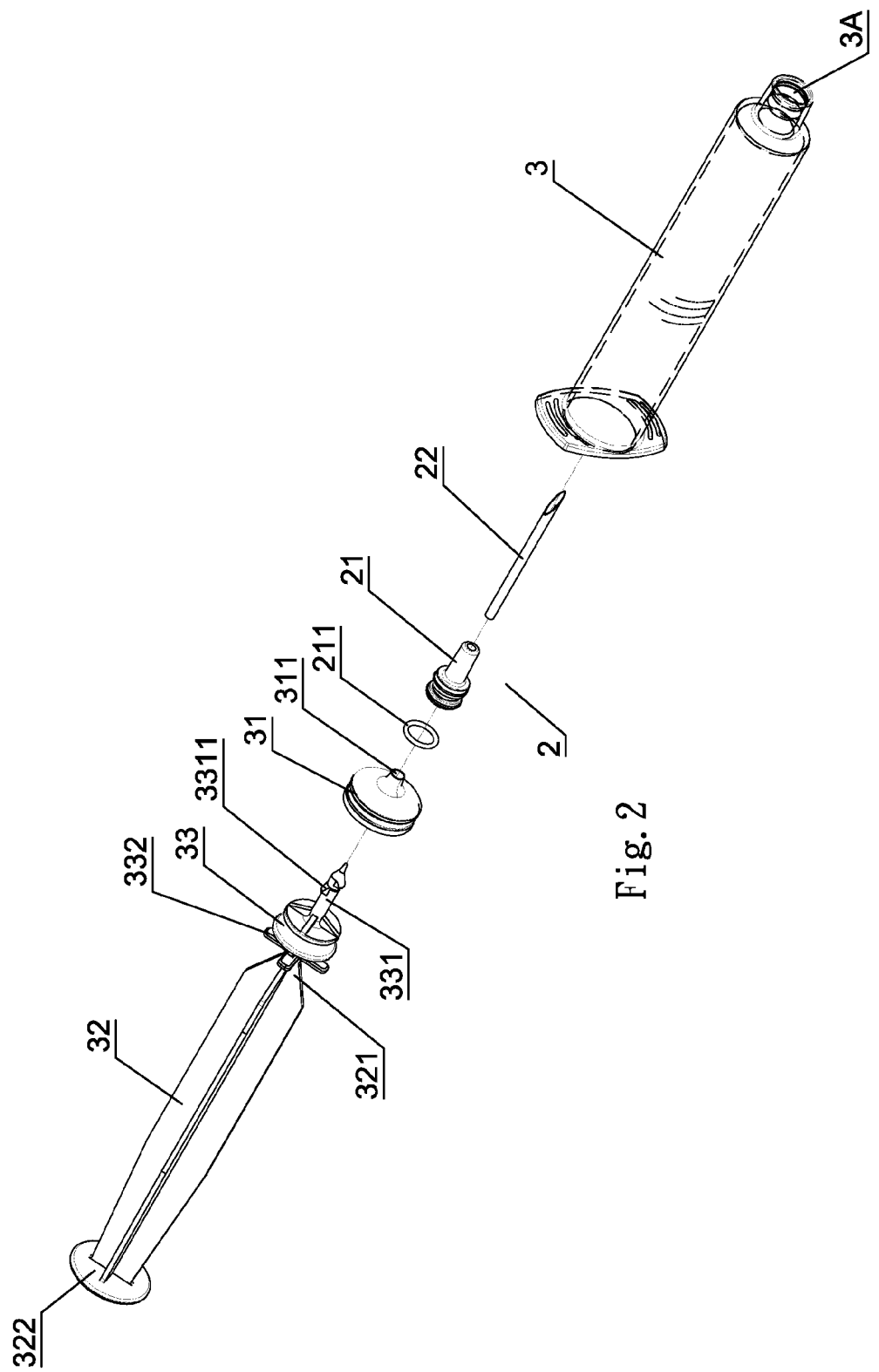
FIG. 2 is an exploded view of the present invention.

As shown in FIG. 1 and FIG. 2, the syringe according to a preferred embodiment of the present invention comprises a needle 2, a barrel 3 and a push rod 32 inserted in the barrel 3.

The needle 2 comprises a needle seat 21 connected to a connection mouth 3A of the barrel 3, a stop ring 211 fitted on an outer wall of the needle seat 21, and a check groove 212 formed on the inner wall of the needle seat 21. The check groove 212 is adapted to engage with a check rib 3311 on a core post 331. A needle body 22 is provided at a front end of the needle seat 21.

A resilient plug 31 is provided in the barrel 3. The resilient plug 31 has a central through hole 311 for insertion of the core post 331 of a push head 33. The push rod 32 includes a press plate 32 at a rear end thereof and a frangible point 321 at a front end thereof. The press plate 32 is adapted for the user to press the push rod 32. The frangible point 321 is adapted for break. The push head 33 is disposed at the front end of the push rod 32 and can be inserted in the resilient plug 31. The push head 33 has a plurality of wing panels 332 at a rear end thereof for easy break. The core post 331 protrudes from a central portion of the push head 33. The check rib 3311 is formed on the outer surface of the core post 331 to engage with the check groove 212 of the needle 2 when pushed in the needle 2. According to the aforesaid structure, the needle body 22 can be retracted in the barrel 3 completely, preventing it from being exposed.

To operate the present invention, as shown in FIG. 3A to FIG. 3D and FIG. 4, after the injection liquid W is drawn in the barrel 3, the elastic plug 31 will be pulled to the rear end of the barrel 3, as shown in FIG. 3A. After injection, the user presses the press plate 33 with his/her thumb, such that the core post 331 at the front end of the push head 33 is pushed into the needle seat 21. The check rib 3311 engages with the check groove 212 to be positioned thereat, as shown in FIG. 3B.

After that, the push rod 32 is pulled backward, so that the push head 33 and the resilient plug 31 bring the need 2 to retract in the barrel 3. The push head 33 is pulled to the rear end of the barrel 3. The resilient plug 31 has an annular protruding portion 312 at a bottom edge thereof to be against the inner wall of the barrel 3. The annular protruding portion 312 has slight resilience to be pushed in an annular recess 34 formed on the inner wall of the rear end of the barrel 3, such that the push rod 32 is positioned thereat, as shown in FIG. 3C.

Figure 4:
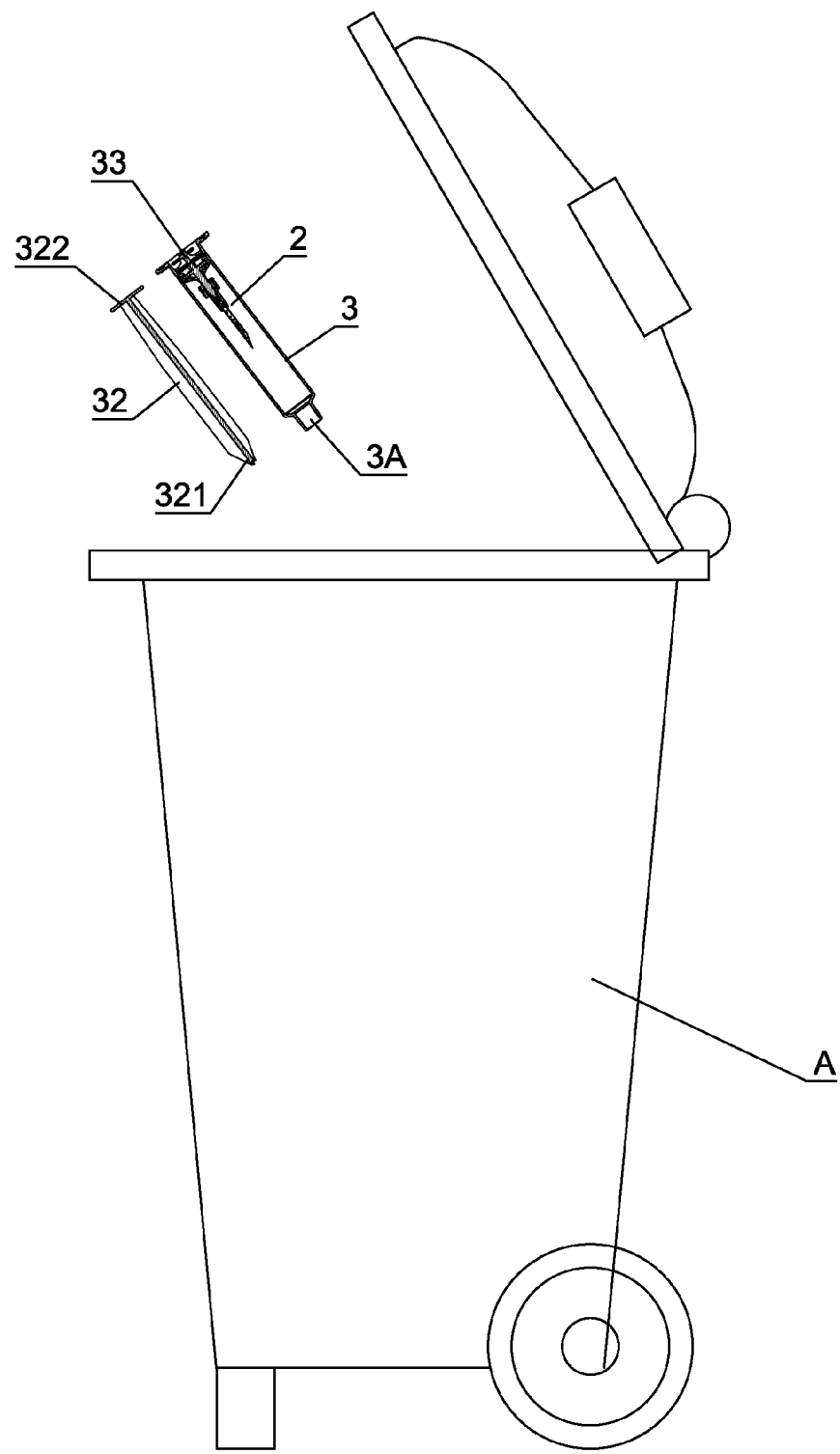
FIG. 4 is a schematic view showing the present invention being thrown in the recycle container.
Figure 5:
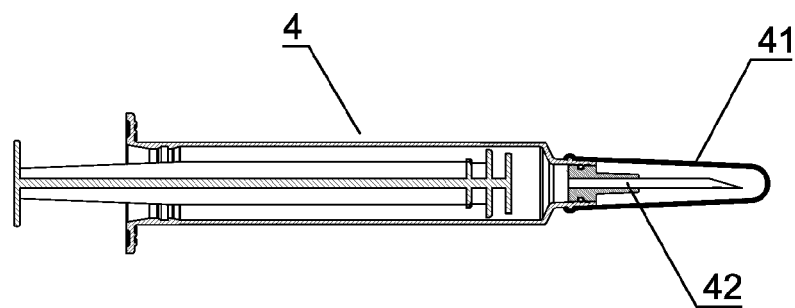
FIG. 5 is a perspective view of a conventional syringe.
Figure 6:
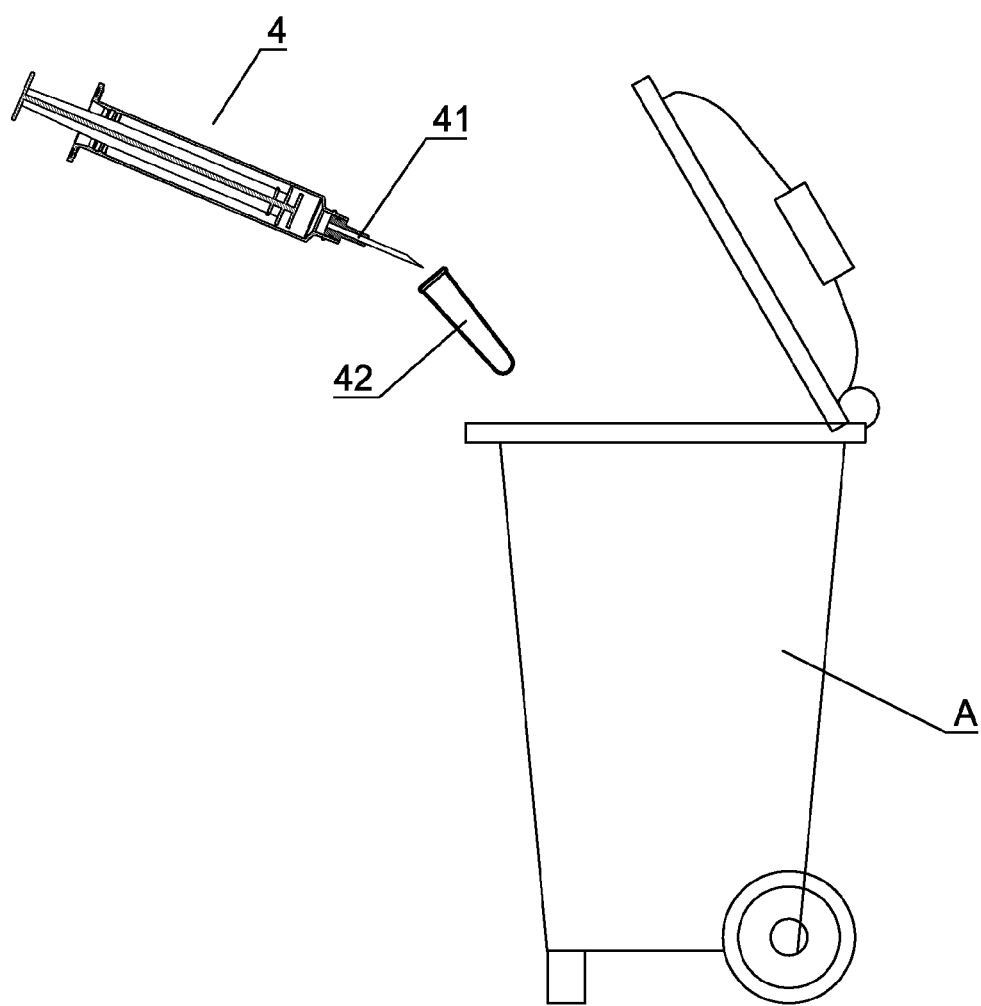
FIG. 6 is a schematic view showing the conventional syringe being thrown in the recycle container.

After the push rod 32 is positioned, the user turns and break the push rod 32 at the frangible point 321, as shown in FIG. 3D. The push rod 32 and the barrel 3 are respectively thrown into the recycle container A, as shown in FIG. 4, so they are disposable for safety. The entire needle 2 is received in the barrel 3 and the rear section of the push rod 32 is broken to separate it from the barrel 3 to be disposed easily.

Although particular embodiments of the present invention have been described in detail for purposes of illustration, various modifications and enhancements may be made without departing from the spirit and scope of the present invention. Accordingly, the present invention is not to be limited except as by the appended claims.

What is claimed is:

1. A syringe, comprising:

a needle, the needle comprising a needle seat connected to a connection mouth, a stop ring fitted on an outer wall of the needle seat and a check groove formed on an inner wall of the needle seat, the check groove being adapted to engage with a check rib, a needle body provided at a front end of the needle seat;

a barrel, the connection mouth being disposed at a front end of the barrel, the barrel having an annular recess formed on an inner wall of a rear end thereof;

a resilient plug, the resilient plug being disposed in the barrel, the resilient plug having a central through hole, the resilient plug having an annular protruding portion at a bottom edge thereof to be against the inner wall of the barrel; and a push rod, the push rod being inserted in the barrel, the push rod including a press plate at a rear end thereof and a frangible point at a front end thereof, a push head provided at the front end of the push rod and inserted in the resilient plug, the push head having a plurality of wing panels at a rear end thereof, a core post protruding from a central portion of the push head and inserted in the through hole of the resilient plug, the check rib being formed on an outer surface of the core post to engage with the check groove of the needle seat when pushed in the needle, wherein when the core post at the front end of the push head is pushed into the needle seat, the check rib engages with the check groove and when the push rod is pulled backward, the annular protruding portion is engaged in the annular recess formed on the inner wall of the rear end of the barrel, such that the push rod is positioned thereat for the user to break the rear section of the push rod at the frangible point to leave the front end of the push rod, the resilient plug and the needle in the barrel.

* * * * *